(12) United States Patent
Sutermeister et al.

(10) Patent No.: US 7,767,726 B2
(45) Date of Patent: Aug. 3, 2010

(54) MEDICAL DEVICES HAVING CROSSLINKED POLYMERIC SURFACES

(75) Inventors: Derek Sutermeister, Eden Prairie, MN (US); Jay Rassat, Buffalo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 278 days.

(21) Appl. No.: 11/801,895

(22) Filed: May 11, 2007

(65) Prior Publication Data

US 2008/0279911 A1 Nov. 13, 2008

(51) Int. Cl.
*A61K 6/083* (2006.01)
(52) U.S. Cl. .................... 522/4; 522/109; 522/160
(58) Field of Classification Search .............. 522/4, 522/109, 160
See application file for complete search history.

(56) References Cited

U.S. PATENT DOCUMENTS

| | | | |
|---|---|---|---|
| 6,545,097 B2 | 4/2003 | Pinchuk et al. | 525/240 |
| 6,777,082 B2 * | 8/2004 | Patel et al. | 428/364 |
| 2002/0147273 A1 * | 10/2002 | Patel et al. | 525/93 |
| 2003/0235602 A1 | 12/2003 | Schwarz | |
| 2004/0202691 A1 | 10/2004 | Richard | 424/423 |
| 2005/0025801 A1 | 2/2005 | Richard | 424/423 |
| 2006/0171981 A1 | 8/2006 | Richard | |
| 2008/0051541 A1 | 2/2008 | Strickler et al. | |
| 2008/0051542 A1 * | 2/2008 | Strickler | 526/273 |

FOREIGN PATENT DOCUMENTS

EP 1449644 8/2004

OTHER PUBLICATIONS

Ron Nickerson, "Plasma Surface Modification for Cleaning and Adhesion," AST Products, Inc., downloaded Dec. 4, 2006 from http://www.astp.com/PDFs/PS_Cleaning_&_Adhesion.pdf.

N.S. Ramesh et al., "Observation of Morphology of Polystyrenic Materials Using Oxygen Plasma Etching" *J. Polym. Sci. Part B: Polym. Phys.*, vol. 29, 1991, pp. 1031-1034.

N. Inagaki, Ph.D., *Plasma Surface Modification and Plasma Polymerization*, Technomic Publishing Company, Inc. © 1996, pp. 24, 35, 38, 50, 51, 56, 57, 66.

Karl J. Hemmerich, "Polymer Materials Selection for Radiation-Sterilized Products", *Medical Device & Diagnostic Industry Magazine*, Feb. 2000, pp. 78-89.

L. Hanley et al., "The growth and modification of materials via ion-surface processing", *Surface Science* 500, 2002, pp. 500-522.

S. Guruvenket et al., "Plasma surface modification of polystyrene and polyethylene," *Applied Surface Science* 236 (1-4), 2004, pp. 278-284.

F.D. Egitto, "Plasma modification of polymer surfaces for adhesion improvement", *IBM J. Res. Develop.*, vol. 38, No. 4, Jul. 1994, pp. 423-439.

S. F. Tead et al., "Polymer diffusion as a probe of damage in ion or plasma etching", *J. Appl. Phys.* 68, No. 6, 1990, pp. 2972-2982.

M.O. Riekerink, "*Structural and Chemical Modification of Polymer Surfaces by Gas Plasma Etching*", Thesis, University of Twente, Enschede, The Netherlands, 2001, Chapters 1 and 2.

Puskas J E et al.: "Synthesis and Characterization of Novel Dendritic (Arborescent, Hyperbranched) Polyisobutylene-Polystyrene Block Copolymers" Journal of Polymer Science, vol. 43, No. 9, May 1, 2005.

* cited by examiner

*Primary Examiner*—Bernard Lipman
(74) *Attorney, Agent, or Firm*—Mayer & Williams PC; David B. Bonham; Keum J. Park

(57) ABSTRACT

According to an aspect of the invention, medical devices are provided which contain at least one polymeric region. The polymeric region contains at least one copolymer, which includes at least one high Tg vinyl aromatic monomer and at least one low Tg monomer. Moreover, the polymeric region contains at least one surface sub-region that is crosslinked and at least one bulk sub-region that is substantially non-crosslinked. According to another aspect of the invention, a method is provided which includes exposing a polymeric region of a medical device to energetic species such that at least one surface sub-region of the polymeric region becomes crosslinked and at least one bulk sub-region remains substantially non-crosslinked. The polymeric region contains at least one copolymer, which includes at least one high Tg vinyl aromatic monomer and at least one low Tg monomer.

25 Claims, 1 Drawing Sheet

MEDICAL DEVICES HAVING CROSSLINKED POLYMERIC SURFACES

FIELD OF THE INVENTION

The present invention relates generally to medical devices, and more particularly to implantable or insertable medical devices having polymeric surfaces.

BACKGROUND OF THE INVENTION

Numerous polymer-based medical devices have been developed for implantation or insertion into the body. For example, various state of the art medical devices consist of a medical device substrate with a polymeric coating that serves as a reservoir for one or more therapeutic agents. Specific examples include drug eluting coronary stents, commercially available from Boston Scientific Corp. (TAXUS®), Johnson & Johnson (CYPHER®) and others, which have become the standard of care for maintaining vessel patency after balloon angioplasty. These products are based on metallic balloon expandable stents with polymeric coatings that release antiproliferative drugs at a controlled rate and total dose effective to inhibit the smooth muscle proliferation that is associated with restenosis (vessel reclosure).

Various types of polymeric materials have been used as drug-releasing reservoirs, including, for example, polystyrene copolymers such as poly(styrene-b-isobutylene-b-styrene) triblock copolymers (SIBS), which are described in U.S. Pat. No. 6,545,097 to Pinchuk et al. In addition to their utility as drug delivery reservoirs, SIBS copolymers have proven valuable for a variety of reasons, including their excellent elasticity, strength, and processability, which characteristics are due, at least in part, to the fact that SIBS copolymers are thermoplastic elastomers. Thermoplastic elastomers are elastomeric (i.e., reversibly deformable) polymers that form so-called "physical crosslinks" which can be reversed, for example, by dissolving or melting the polymer.

SUMMARY OF THE INVENTION

According to an aspect of the invention, medical devices are provided which contain at least one polymeric region. The polymeric region (which may correspond, for example, to an entire device, a discrete device component or a coating, among other possibilities) contains at least one copolymer, which includes at least one high Tg vinyl aromatic monomer and at least one low Tg monomer. Moreover, the polymeric region includes at least one surface sub-region that is crosslinked and at least one bulk sub-region that is substantially non-crosslinked.

According to another aspect of the invention, a method is provided which includes exposing a polymeric region of a medical device to energetic species such that at least one surface sub-region of the polymeric region becomes crosslinked, and such that there remains a bulk sub-region that is substantially non-crosslinked. As above, the polymeric region contains at least one copolymer, which includes at least one high Tg vinyl aromatic monomer and at least one low Tg monomer.

This is advantageous, for example, in that medical devices having polymeric regions may be provided, in which the chemical and/or mechanical properties of the surface are substantially modified, whereas those of the bulk is not.

These and other aspects and embodiments of the present invention, as well as various advantages, will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

According to an aspect of the invention, medical devices are provided which contain at least one polymeric region. The polymeric region contains at least one copolymer, which includes at least one high Tg vinyl aromatic monomer and at least one low Tg monomer. Moreover, the polymeric region includes at least one surface sub-region that is crosslinked and at least one bulk sub-region that is substantially non-crosslinked.

As used herein, a "sub-region" is a portion of a polymeric region whose properties (e.g., crosslinking density) differ from those of another portion of the region.

As used herein a "crosslinked" sub-region is one that is covalently crosslinked. Whether or not a surface sub-region is crosslinked can be determined by methods such as atomic force microscopy (AFM), spectroscopy methods, or friction measurement, among others.

Typical depths of crosslinking may range, for example, from 1 nm to 10 nm to 100 nm to 1 micron to 10 microns to 100 microns to 1 mm to 2 mm, depending on the technique that is employed.

As used herein, a given bulk sub-region is "substantially non-crosslinked" where crosslinking is not detectable in the sub-region or where the crosslinking density, if detectable, is less than or equal to 5% of the crosslinking density at the surface, for ranging from 5% to 2% to 1% or less.

This is advantageous, for example, in that medical devices having polymeric regions may be provided, in which the chemical and/or mechanical properties of the surface are substantially modified, whereas those of the bulk is not. This advantage may be better understood upon review of the specific embodiment of the invention described below in conjunction with FIGS. 1A and 1B.

Figure 1A:
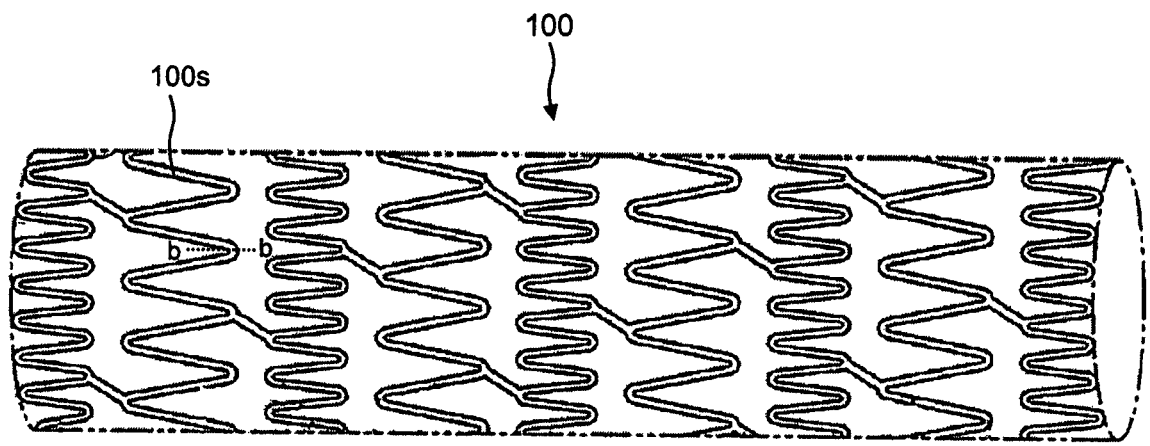
FIG. 1A is a schematic perspective view of a stent in accordance with an embodiment of the present invention.
Figure 1B:
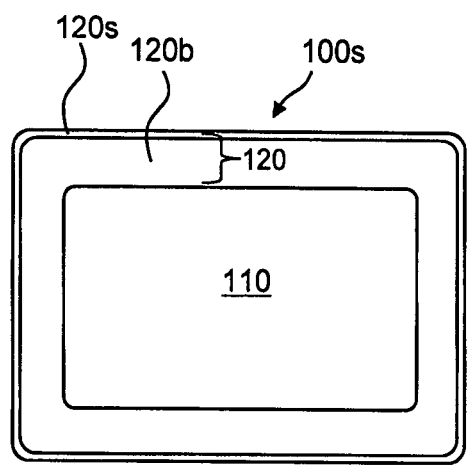
FIG. 1B is a schematic cross-sectional view of a portion of the stent of FIG. 1A, taken along line b-b.

While the particular embodiment of FIGS. 1A and 1B is directed to a vascular stent, examples of medical devices for the practice of the present invention vary widely and include implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglilmi detachable coils and metal coils), septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, fins and fusion devices, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other devices that are implanted or inserted into the body and from which therapeutic agent is released.

As noted above, medical devices provided in accordance with the present invention contain at least one polymeric region, which comprises at least one surface sub-region that is crosslinked and at least one bulk sub-region that is substantially non-crosslinked. The bulk sub-region may be disposed, for example, beneath the surface sub-region, or the surface sub-region may be disposed, for example, beneath the bulk sub-region, among other possible spatial relationships.

In some embodiments, the polymeric regions of the present invention correspond to an entire medical device. In other embodiments, the polymeric regions correspond to one or more portions of a medical device. For instance, the polymeric regions can be in the form of discrete medical device components, in the form of one or more fibers which are incorporated into a medical device, in the form of one or more polymeric layers formed over all or only a portion of an underlying substrate, and so forth. Materials for use as underlying medical device substrates include ceramic, metallic and polymeric substrates, as well as substrates formed from hybrids of these materials. Layers can be provided over an underlying substrate at a variety of locations and in a variety of shapes (e.g., in the form of a series of rectangles, stripes, or any other continuous or non-continuous pattern). As used herein a "layer" of a given material is a region of that material whose thickness is small compared to both its length and width. As used herein a layer need not be planar, for example, taking on the contours of an underlying substrate. Layers can be discontinuous (e.g., patterned).

As used herein, a "polymeric region" is a region (e.g., an entire device, a device component, a device coating layer, etc.) that contains polymers, for example, from 50 wt % or less to 75 wt % to 90 wt % to 95 wt % to 97.5 wt % to 99 wt % or more polymers.

As used herein, "polymers" are molecules containing multiple copies (e.g., from 2 to 5 to 10 to 25 to 50 to 100 to 250 to 500 to 1000 or more copies) of one or more constitutional units, commonly referred to as monomers. As used herein, the term "monomers" may refer to the free monomers and those that are incorporated into polymers, with the distinction being clear from the context in which the term is used.

Polymers may take on a number of configurations, which may be selected, for example, from cyclic, linear and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), networked configurations (e.g., crosslinked configurations), and so forth.

As used herein, "homopolymers" are polymers that contain multiple copies of a single constitutional unit. "Copolymers" are polymers that contain multiple copies of at least two differing constitutional units (i.e., monomers), examples of which include random, statistical, gradient, periodic (e.g., alternating) and block copolymers.

As used herein, "block copolymers" are copolymers that contain two or more polymer blocks that differ in composition, for instance, because a constitutional unit (i.e., a monomer) is found in one polymer block that is not found in another polymer block. As used herein, a "polymer block" or "block" is a grouping of constitutional units (e.g., 5 to 10 to 25 to 50 to 100 to 250 to 500 to 1000 or more units). Blocks can be unbranched or branched. Blocks can contain a single type of constitutional unit (also referred to herein as "homopolymeric blocks") or multiple types of constitutional units (also referred to herein as "copolymeric blocks") which may be present, for example, in a random, statistical, gradient, or periodic (e.g., alternating) distribution.

As used herein, a "chain" is a linear polymer or a portion thereof, for example, a linear block.

As noted above, the polymeric regions of the present invention include at least one copolymer, which includes at least one high Tg vinyl aromatic monomer and at least one low Tg monomer. In certain embodiments, copolymer contains (a) at least one high Tg polymer block that contains at least one high Tg vinyl aromatic monomer and (b) at least one low Tg polymer block that contains at least one low Tg monomer.

A "low $T_g$ polymer block" is a polymer block that displays a glass transition temperature ($T_g$), as measured by any of a number of techniques such as differential scanning calorimetry (DSC), that is below body temperature, typically from 37° C. to 35° C. to 30° C. to 25° C. to 0° C. to −25° C. to −50° C. or below. "Body temperature" will depend upon the subject being treated and averages 37° C. for humans. As a result of their low glass transition temperatures, low $T_g$ polymer blocks are typically soft and elastomeric at body temperature. A "low $T_g$ monomer" is a monomer that, when in homopolymer form, displays a glass transition temperature ($T_g$) that is below body temperature, more typically from 37° C. to 35° C. to 30° C. to 25° C. to 0° C. to −25° C. to −50° C. or below.

Conversely, a "high $T_g$ polymer block" is a polymer block that displays a glass transition temperature which is above body temperature, typically from 37° C. to 40° C. to 45° C. to 50° C. to 60° C. to 75° C. to 100° C. or above. As a result of their high glass transition temperatures, high $T_g$ polymer blocks are typically hard and rigid at body temperature. A "high $T_g$ monomer" is a monomer that, when in homopolymer form, displays a glass transition temperature ($T_g$) that is above body temperature, typically from 37° C. to 40° C. to 45° C. to 50° C. to 60° C. to 75° C. to 100° C. or above.

Examples of block copolymer structures for use in the present invention include (a) block copolymers having alternating blocks of the type $(HL)_m$, $L(HL)_m$ and $H(LH)_m$ where L is a low $T_g$ polymer block, H is a high $T_g$ polymer block, m is a positive whole number of 1 or more, and (b) block copolymers having multi-arm geometries, such as $X(LH)_n$, and $X(HL)_n$, where n is a positive whole number of 2 or more and X is a hub species (e.g., an initiator molecule residue, a residue of a molecule to which preformed polymer chains are attached, etc.) Note that hub species and other non-polymer-chain species are generally ignored in describing block copolymers. For example, $X(LH)_2$ is generally designated as an HLH triblock copolymer. Examples of other non-polymer-chain species, which are commonly present in copolymers, include capping molecules, and linking residues. Other examples of block copolymers include comb copolymers having an L chain backbone and multiple H side chains, as well as comb copolymers having an H chain backbone and multiple L side chains.

Specific examples of high Tg polymer blocks include homopolymer and copolymer blocks containing one or more types of vinyl aromatic monomers including, for example, those selected from the following (listed along with published Tg's for homopolymers of the same): (1) unsubstituted vinyl aromatics, such as styrene (Tg 100° C.) and 2-vinyl naphthalene (Tg 151° C.), (2) vinyl substituted aromatics such as alpha-methyl styrene, and (3) ring-substituted vinyl aromatics including (a) ring-alkylated vinyl aromatics such as 3-methylstyrene (Tg 97° C.), 4-methylstyrene (Tg 97° C.), 2,4-dimethylstyrene (Tg 112° C.), 2,5-dimethylstyrene (Tg 143° C.), 3,5-dimethylstyrene (Tg 104° C.), 2,4,6-trimethylstyrene (Tg 162° C.), and 4-tert-butylstyrene (Tg 127° C.), (b) ring-alkoxylated vinyl aromatics, such as 4-methoxystyrene (Tg 113° C.) and 4-ethoxystyrene (Tg 86° C.), (c) ring-halogenated vinyl aromatics such as 2-chlorostyrene (Tg 119° C.), 3-chlorostyrene (Tg 90° C.), 4-chlorostyrene (Tg 110° C.), 2,6-dichlorostyrene (Tg 167° C.), 4-bromostyrene (Tg 118° C.) and 4-fluorostyrene (Tg 95° C.), (d) ring-ester-substituted vinyl aromatics such as 4-acetoxystyrene (Tg 116° C.), (e) ring-hydroxylated vinyl aromatics such as 4-hydroxystyrene (Tg 174° C.), (f) ring-amino-substituted vinyl aromatics including 4-amino styrene, and (g) ring-silyl-substituted styrenes, (4) unsubstituted and substituted vinyl pyridines such as 2-vinyl pyridine (Tg 104° C.) and 4-vinyl pyridine (Tg 142° C.), and (5) other vinyl aromatic monomers such as vinyl carbazole (Tg 227° C.) and vinyl ferrocene (Tg 189° C.). High Tg blocks in accordance with the present invention may also contain monomers in addition to high Tg vinyl aromatic monomers including high Tg vinyl esters, high Tg vinyl amines, high Tg vinyl halides, high Tg alkyl vinyl ethers, high Tg acrylic monomers, and high Tg methacrylic monomers, among others.

Specific examples of low Tg polymer blocks include homopolymer and copolymer blocks containing one or more of the following: (1) unsubstituted and substituted alkene monomers including ethylene, propylene (Tg −8 to −13° C.), isobutylene (Tg −73° C.), 1-butene (Tg −24° C.), 4-methyl pentene (Tg 29° C.), 1-octene (Tg −63° C.) and other α-olefins, dienes such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, and 3-butyl-1,3-octadiene, and halogenated alkene monomers including vinylidene chloride (Tg −18° C.), vinylidene fluoride (Tg −40° C.), cis-chlorobutadiene (Tg −20° C.), and trans-chlorobutadiene (Tg −40° C.); (2) acrylic monomers including: (a) alkyl acrylates such as methyl acrylate (Tg 10° C.), ethyl acrylate (Tg −24° C.), propyl acrylate, isopropyl acrylate (Tg −11° C., isotacetic), butyl acrylate (Tg −54° C.), sec-butyl acrylate (Tg −26° C.), isobutyl acrylate (Tg −24° C.), cyclohexyl acrylate (Tg 19° C.), 2-ethylhexyl acrylate (Tg −50° C.), and dodecyl acrylate (Tg −3° C.), (b) arylalkyl acrylates such as benzyl acrylate (Tg 6° C.), (c) alkoxyalkyl acrylates such as 2-ethoxyethyl acrylate (Tg −50° C.) and 2-methoxyethyl acrylate (Tg −50° C.), (d) halo-alkyl acrylates such as 2,2,2-trifluoroethyl acrylate (Tg −10° C.) and (e) cyano-alkyl acrylates such as 2-cyanoethyl acrylate (Tg 4° C.); (3) methacrylic monomers including (a) alkyl methacrylates such as butyl methacrylate (Tg 20° C.), hexyl methacrylate (Tg −5° C.), 2-ethylhexyl methacrylate (Tg −10° C.), octyl methacrylate (Tg −20° C.), dodecyl methacrylate (Tg −65° C.), hexadecyl methacrylate (Tg 15° C.) and octadecyl methacrylate (Tg −100° C.) and (b) aminoalkyl methacrylates such as diethylaminoethyl methacrylate (Tg 20° C.) and 2-tert-butylaminoethyl methacrylate (Tg 33° C.); (4) vinyl ether monomers including (a) alkyl vinyl ethers such as methyl vinyl ether (Tg −31° C.), ethyl vinyl ether (Tg −43° C.), propyl vinyl ether (Tg −49° C.), butyl vinyl ether (Tg −55° C.), isobutyl vinyl ether (Tg −19° C.), 2-ethylhexyl vinyl ether (Tg −66° C.) and dodecyl vinyl ether (Tg −62° C.); (5) cyclic ether monomers include tetrahydrofuran (Tg −84° C.), trimethylene oxide (Tg −78° C.), ethylene oxide (Tg −66° C.), propylene oxide (Tg −75° C.), methyl glycidyl ether (Tg −62° C.), butyl glycidyl ether (Tg −79° C.), allyl glycidyl ether (Tg −78° C.), epibromohydrin (Tg −14° C.), epichlorohydrin (Tg −22° C.), 1,2-epoxybutane (Tg −70° C.), 1,2-epoxyoctane (Tg −67° C.) and 1,2-epoxydecane (Tg −70° C.); (6) ester monomers (other than the above acrylates and methacrylates) including ethylene malonate (Tg −29° C.), vinyl acetate (Tg 30° C.), and vinyl propionate (Tg 10° C.); and (7) siloxane monomers including dimethylsiloxane (Tg −127° C.), diethylsiloxane, methylethylsiloxane, methylphenylsiloxane (Tg −86° C.), and diphenylsiloxane.

As used herein, a "poly(vinyl aromatic) block" is a polymer block that contains multiple copies of one or more types of vinyl aromatic monomers, a "polyalkene block" is a block that contains multiple copies of one or more types of alkene monomers, and so forth.

As will be appreciated by those of ordinary skill in the art, the copolymers employed in accordance with the present invention may be synthesized according to known methods, including cationic, anionic, and radical polymerization methods, among others, particularly controlled/"living" cationic, anionic and radical polymerizations, as well as combinations of the same.

In addition to at least one vinyl aromatic copolymer, the polymeric regions for use in the medical devices of the present invention may optionally contain one or more supplemental polymers. Examples of supplemental polymers include various homopolymers and copolymers (including alternating, random, statistical, gradient and block copolymers), which may be cyclic, linear, or branched (e.g., the polymers may have star, comb or dendritic architecture), which may be natural or synthetic, and which may be biostable or biodegradable.

The polymeric regions for use in the medical devices of the present invention may further contain at least one therapeutic agent, numerous examples of which are set forth below.

One specific embodiment of the invention will now be described in conjunction with the drawings. FIG. 1A is a schematic perspective view of stent 100 which contains a number of interconnected struts 100s. FIG. 1B is a schematic cross-sectional view (not to scale) taken along line b-b of strut 110s of stent 100 of FIG. 1A, and shows a metallic stent substrate 110 and a polymeric coating region 120, which encapsulates the substrate 110 and which comprises a surface sub-region 120s that is crosslinked, beneath which is a bulk sub-region 120b that is substantially non-crosslinked. Although the crosslinked sub-region 210s is shown adjacent to the substantially non-crosslinked bulk sub-region 120b in the embodiment shown, there will generally be a transition region between the sub-regions 120s, 120b. The abruptness of the transition between the adjacent crosslinked and substantially non-crosslinked sub-regions 210s, 120b will generally be a function of the processing conditions employed. The polymeric coating 120 may contain, for example, a SIBS copolymer, which is crosslinked in surface sub-region 120s.

The polymeric coating 120 may further contain, for example, an antiproliferative agent such as paclitaxel to combat restenosis.

As noted above, SIBS is a thermoplastic elastomer that forms so-called "physical crosslinks" which can be reversed, for example, by dissolving or melting the polymer. In this regard, SIBS is a triblock copolymer having a soft, elastomeric low Tg midblock and hard high Tg endblocks. As with many block copolymers, SIBS tends to phase separate, with the elastomeric blocks aggregating to form elastomeric phase domains and the hard blocks aggregating to form hard phase domains. It has been hypothesized that, because each elastomeric block has a hard block at each end, and because different hard blocks within the same triblock copolymer are capable of occupying two different hard phase domains, the hard phase domains become "physically crosslinked" to one another via the soft blocks. Regardless, of the underlying molecular basis, SIBS has excellent elasticity, strength, and processability. For example, the coating of the stent of FIGS. 1A and 1B is readily applied to the stent substrate using solvent-based techniques (e.g. spraying) and is well-secured to the stent substrate due to the encapsulation that occurs during processing and to the inherent strength of SIBS. Moreover, being elastomeric, the coating readily deforms as the stent is expanded/deployed within a blood vessel in vivo. The polyisobutylene low Tg block, which gives SIBS it elasticity, is also significantly more tacky that the polystyrene hard blocks. Surface tack is an important property for stent coatings, as high surface tack can cause defects in the coating when the stent is expanded/deployed in vivo. By crosslinking the SIBS coating at its surface in accordance with the present invention, the surface properties of the SIBS coating are modified (i.e., the surface tack is reduced) whereas the bulk properties of the SIBS coating are substantially unchanged.

"Therapeutic agents," "drugs," "pharmaceutically active agents,""pharmaceutically active materials," and other related terms may be used interchangeably herein. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition). Numerous therapeutic agents are described here.

Exemplary therapeutic agents for use in conjunction with the present invention include the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naffidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Particularly beneficial therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

A wide range of therapeutic agent loadings may be used in conjunction with the medical devices of the present invention. Typical loadings range, for example, from 1 wt % or less to 2 wt % to 5 wt % to 10 wt % to 25 wt % or more of the polymeric region.

Numerous techniques are available for forming polymeric regions in accordance with the present invention.

For example, where a polymeric region is formed from one or more polymers having thermoplastic characteristics, a variety of standard thermoplastic processing techniques may be used to form the polymeric region. Using these techniques, a polymeric region can be formed, for instance, by (a) first providing a melt that contains polymer(s) and any supplemental agents such as therapeutic agent(s) and (b) subsequently cooling the melt. Examples of thermoplastic processing techniques, including compression molding, injection molding, blow molding, spraying, vacuum forming and calendaring, extrusion into sheets, fibers, rods, tubes and other cross-sectional profiles of various lengths, and combinations of these processes, among others. Using these and other thermoplastic processing techniques, entire devices or portions thereof can be made.

Other processing techniques besides thermoplastic processing techniques may also be used to form the polymeric regions of the present invention, including solvent-based techniques. Using these techniques, a polymeric region can be formed, for instance, by (a) first providing a solution or dispersion that contains polymer(s) and any supplemental agents such as therapeutic agent(s) and (b) subsequently removing the solvent. The solvent that is ultimately selected will contain one or more solvent species, which are generally selected based on their ability to dissolve at least one of the polymer(s) that form the polymeric region, in addition to other factors, including drying rate, surface tension, etc. In certain embodiments, the solvent is selected based on its ability to dissolve any supplemental agents such as therapeutic agent(s) as well. Thus, the therapeutic agent and any other supplemental agents may be dissolved or dispersed in the coating solution. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes, among others.

In some embodiments of the invention, a polymer containing solution (where solvent-based processing is employed) or a polymer melt (where thermoplastic processing is employed) is applied to a substrate to form a polymeric region. For example, the substrate can correspond to all or a portion of an implantable or insertable medical device to which a polymeric coating is applied, for example, by spraying, extrusion, and so forth. The substrate can also be, for example, a template, such as a mold, from which the polymeric region is removed after solidification. In other embodiments, for example, extrusion and co-extrusion techniques, one or more polymeric regions are formed without the aid of a substrate. In a specific example, an entire medical device is extruded. In another, a polymeric coating layer is co-extruded along with an underlying medical device body.

According to an aspect of the invention, a method is provided which includes exposing a polymeric region of a medical device to energetic species, such that at least one surface sub-region of the polymeric region becomes crosslinked, beneath which is a bulk sub-region that is substantially non-crosslinked. As above, the polymeric region contains at least one copolymer, which includes at least one high Tg vinyl aromatic monomer and at least one low Tg monomer.

As previously indicated, this is advantageous, for example, in that polymeric regions may be provided in which the mechanical and/or chemical properties of the surface are substantially modified, whereas those of the bulk are not. Accordingly, the present invention does not employ bulk chemical crosslinking techniques or bulk crosslinking techniques that employ high energy/ionizing radiation, such as gamma rays, X rays, and electron beams.

Without wishing to be bound by theory, it is believed that various energetic species are able to cause radicals to form in polymers (e.g., by removing hydrogen atoms from the polymer), which radicals may then undergo chain scission or crosslinking. See, e.g., N. Inagaki, Ph.D., *Plasma Surface Modification and Plasma Polymerization*, Technomic Publishing Company, Inc. © 1996, p. 24. Some polymers are known to preferentially undergo crosslinking, while other polymers preferentially undergo chain scission. For example, it has been observed that, for polymers with carbon-carbon backbones, cross-linking generally will occur if the carbons have one or more hydrogen atoms attached, whereas chain-scission generally occurs at tetra-substituted carbons. See, e.g., "Polymer Materials Selection for Radiation-Sterilized Products" by Karl J. Hemmerich, *Medical Device & Diagnostic Industry Magazine*, February 2000, pp. 78-89.

In some embodiments, the surface of the polymeric region is crosslinked by bombarding it with photons, particularly ultraviolet (UV) photons, for example, selected from UV-A (320-400 nm), UV-B (320 to 280 nm) and UV-C (280 to 200 nm). The dosage of the photons will vary depending on the application, and can be determined by those of ordinary skill in the art.

For example, and without wishing to be bound by theory, exposure of polystyrene to UV irradiation has been reported to result in C—H bond cleavage in polystyrene, leading to the formation of mid-chain benzyl-type radicals,

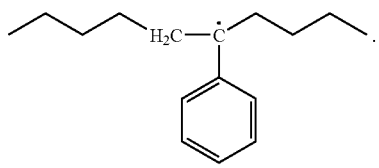

See, e.g., N. Inagaki, Ph.D., *Plasma Surface Modification and Plasma Polymerization*, at p. 51. The recombination of two such radicals on adjacent chains results in crosslinking.

The process of C—H bond cleavage upon UV irradiation may be augmented in some embodiments of the invention by employing a hydrogen abstracting photoinitiator, for example, benzophenone. Id. at pp. 56-57. Other known aromatic ketones may also be used for this purpose, including isopropyl thioxanthone, anthraquinone, acetophenone, benzyl and xanthone, among others. For example, one or more of the foregoing photoinitiators may be dissolved in a solvent and applied to the surface of a polymeric region. Under UV irradiation, these initiators abstract hydrogen from polymers at the polymeric region surface, thereby forming polymer radicals which lead to crosslinking.

In some embodiments, the surface of the polymeric region is crosslinked by bombarding it with ions, for example, ions of one or more inert species (e.g., nitrogen, helium, argon, etc.).

For example, in some embodiments, the polymeric region is crosslinked by ion implantation. As noted in L. Hanley et al., *Surface Science* 500 (2002) 500-522, ion implantation with inert species is known to lead to hard, crosslinked surfaces while at the same time maintaining the bulk properties of the material. Increasing the implantion energy has been reported to result in increased penetration depth, but not an increase in the amount of crosslinking. Id. Ion implantation has been used to harden polystyrene, among other polymers. Id.

In some embodiments, the polymeric region is crosslinked by plasma processing. Plasmas are ionized gases, which can contain ions, electrons and neutral species. Plasma processing of polymers is normally carried out at sub-atmospheric pressures, which allows processing to be conducted at lower temperatures than atmospheric-pressure plasmas (e.g., near room temperature, in some cases). Moreover, the use of a vacuum chamber allows one to tightly control the gases from which the plasma is formed. Plasmas are usually generated by applying an energy field at a given frequency. Plasmas include radiofrequency plasmas (e.g., capacitively coupled plasmas, inductively coupled plasmas, helicon plasmas, etc.) and microwave plasmas (e.g., electron cyclotron resonance plasmas, etc.), among others. The characteristics of a given plasma are dictated by a number of factors including the working gas for the plasma (e.g., whether the gas is an inert gas such as nitrogen, helium or argon, or whether it is a reactive gas such as oxygen), the working gas flow rate, the discharge power (an increase of which may increase, for example, the density and velocity of ions in the plasma), the pressure (an increase in which may, for example, increase gas concentration, decrease electron density, and decrease the energy of ions impinging on the substrate), among other factors. In some cases, a bias is applied to enhance the bombardment of the substrate surface with the ions.

Various energetic species are associated with plasmas, including ions, electrons and photons (including UV photons). Where the magnitude of the energy transfer from the plasma is higher than the binding energy of certain orbital electrons in the polymer, the polymer will be ionized, leading to molecular fragmentation into small fragments that contain free radicals. Where the magnitude of the energy transfer from the plasma is lower than the binding energy, on the other hand, certain electrons in the polymer are raised to an excited upper orbital, followed by dissociation, producing radicals at the polymer surface (see, e.g., N. Inagaki, Ph.D., *Plasma Surface Modification and Plasma Polymerization*, at pp. 56-57, which as noted above, can lead to crosslinking. Crosslinking in a plasma that employs an inert gas is sometimes referred to as CASING (i.e., crosslinking via activated species of inert gases). Because only the surface properties are altered, the plasma treatment times may be relatively short.

In this regard, S. Guruvenket et al., "Plasma surface modification of polystyrene and polyethylene," *Applied Surface Science* 2004, 236(1-4) 278-284, describe the treatment of polystyrene with an argon plasma that was generated using Microwave Electron Cyclotron Resonance (ECR). The exposure of the polymer to the inert gas plasma was reported to be sufficient to abstract hydrogen and to form surface free radicals, which then form crosslinks or cause chain scission, as noted above. Low molecular-weight materials were believed to be either removed by that plasma or converted by the plasma to high-molecular weight products by cross-linking reactions.

It has been proposed that for plasma modification of polystyrene in the absence of ion bombardment, the ratio of chain scission to crosslinking events occurring during treatment is much greater than for modification performed in the presence of ion bombardment. See F. D. Egitto, *IBM J. Res. Develop.*, Vol. 38, No. 4 July, 1994, 423-439 and S. F. Tead et al. *J. Appl. Phys.* 68, No. 6, 2972 (1990). As noted above, it is known to apply a bias in order to bombard substrates with ions during plasma processing.

As previously indicated, when exposed to energetic species, certain polymers, such as polystyrene, predominantly undergo crosslinking. Other polymers, for example, those having tetra-substituted carbons with no hydrogen atoms attached, such as polyisobutylene, predominantly undergo chain scission. Thus, in certain embodiments, for example, those where a polymeric region containing SIBS (which contains polystyrene and polyisobutylene blocks) is processed, crosslinking of the polystyrene regions may occur, while chain breakdown and associated etching of the polyisobutylene regions may occur. Both effects are expected to decrease the surface tack of the polymeric region.

Thus, in some embodiments, one or more blocks of a block copolymer is/are preferentially etched relative one or more other blocks. For example, the polyisobutylene phase domains within SIBS may be preferentially etched using a reactive plasma gas, which also acts to crosslink the polystyrene phase domains.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising a polymeric region that comprises a copolymer, said copolymer comprising a high Tg vinyl aromatic monomer and a low Tg monomer, and said polymeric region comprising a surface sub-region that is crosslinked and a bulk sub-region that is substantially non-crosslinked, wherein the medical device further comprises a therapeutic agent.

2. The medical device of claim 1, wherein the low Tg monomer is an alkene monomer.

3. The medical device of claim 1, wherein the copolymer is a block copolymer that comprises a high Tg block that comprises the vinyl aromatic monomer and a low Tg polymer block that comprises the low Tg monomer.

4. The medical device of claim 3, wherein the low Tg monomer is an alkene monomer.

5. A medical device comprising a polymeric region that comprises a block copolymer, wherein said block copolymer comprises a high Tg block that comprises a vinyl aromatic monomer and a low Tg polymer block that comprises a low Tg monomer, wherein the vinyl aromatic monomer is styrene and the low Tg monomer is isobutylene, and wherein said polymeric region comprises a surface sub-region that is crosslinked and a bulk sub-region that is substantially non-crosslinked.

6. The medical device of claim 5, wherein the copolymer is a poly(styrene-b-isobutylene-b-styrene) triblock copolymer.

7. A medical device comprising a polymeric region that comprises a copolymer, said copolymer comprising a high Tg vinyl aromatic monomer and a low Tg monomer, and said polymeric region comprising a surface sub-region that is crosslinked and a bulk sub-region that is substantially non-crosslinked, wherein the surface sub-region extends to a depth of 1 µm or less.

8. The medical device of claim 1, wherein the polymeric region is a polymeric coating that is disposed on an underlying substrate.

9. A medical device comprising a polymeric region that comprises a copolymer, said copolymer comprising a high Tg vinyl aromatic monomer and a low Tg monomer, and said polymeric region comprising a surface sub-region that is crosslinked and a bulk sub-region that is substantially non-crosslinked, wherein medical device is a stent.

10. The medical device of claim 1, wherein the therapeutic agent is an antiproliferative agent.

11. The medical device of claim 1, wherein the therapeutic agent is paclitaxel.

12. The medical device of claim 1, wherein the polymeric region is a polymeric coating that is disposed on an underlying stent substrate and comprises a poly(styrene-b-isobutylene-b-styrene) triblock copolymer and an antiproliferative agent.

13. The medical device of claim 1, wherein the medical device is formed by a method comprising exposing the polymeric region of the medical device to energetic species such that the surface sub-region within the polymeric region becomes crosslinked and the bulk sub-region beneath the surface sub-region, relative to a source of said energetic species, is not substantially crosslinked.

14. The medical device of claim 13, wherein said method reduces surface tack of said medical device.

15. The medical device of claim 13, wherein the energetic species comprise photons.

16. The medical device of claim 15, wherein the photons have a wavelength ranging from 200 nm to 320 nm.

17. The medical device of claim 16, wherein a hydrogen abstracting photoinitiator is applied to the surface of said polymeric region before exposing the polymeric region to the photons.

18. The medical device of claim 17, wherein the hydrogen abstracting photoinitiator is an aromatic ketone selected from benzophenone, isopropyl thioxanthone, anthraquinone, acetophenone, benzil, xanthone, and combinations thereof.

19. The medical device of claim 13, wherein the wherein the energetic species are inert ions.

20. The medical device of claim 19, wherein the inert ions are selected from nitrogen ions, helium ions, argon ions, and combinations thereof.

21. The medical device of claim 19, wherein the polymeric region is bombarded in an ion implantation process.

22. The medical device of claim 13, wherein the energetic species comprise photons and ions.

23. The medical device of claim 22, wherein the polymeric region is exposed to a plasma that comprises inert ions that are formed using an inert working gas.

24. The medical device of claim 23, wherein the working gas is selected from nitrogen, helium, argon and combinations thereof.

25. The medical device of claim 23, wherein the ions are accelerated into surface of the polymeric region.

* * * * *